(12) United States Patent
Porter et al.

(10) Patent No.: US 8,936,364 B2
(45) Date of Patent: Jan. 20, 2015

(54) WAVEFRONT SENSORLESS ADAPTIVE CORRECTION OF THE WAVE ABERRATION FOR AN EYE

(71) Applicant: University of Houston System, Houston, TX (US)

(72) Inventors: Jason Porter, Manvel, TX (US); Heidi Hofer, Houston, TX (US); Nripun Sredar, Houston, TX (US); Hope Queener, Houston, TX (US); Chaohong Li, Suzhou (CN); Lukasz Sterkowicz, Cracow (PL)

(73) Assignee: University of Houston System, Houston, TX (US)

( * ) Notice: Subject to any disclaimer, the term of this patent is extended or adjusted under 35 U.S.C. 154(b) by 183 days.

(21) Appl. No.: 13/656,380

(22) Filed: Oct. 19, 2012

(65) Prior Publication Data

US 2013/0100405 A1 Apr. 25, 2013

Related U.S. Application Data

(60) Provisional application No. 61/549,438, filed on Oct. 20, 2011.

(51) Int. Cl.
*A61B 3/14* (2006.01)
*A61B 3/10* (2006.01)
*A61B 3/00* (2006.01)

(52) U.S. Cl.
CPC ............... *A61B 3/1015* (2013.01); *A61B 3/00* (2013.01); *A61B 3/14* (2013.01)
USPC .......................................... 351/206; 351/205

(58) Field of Classification Search
CPC ...... A61B 3/14; A61B 3/1015; A61B 3/1025; A61B 3/12; A61B 3/102; A61B 3/1225; A61B 3/0025; A61B 3/103; A61B 3/107; A61B 3/0091; A61B 3/10; A61B 3/0008; A61B 3/0075; A61B 3/1241
USPC .......... 351/200, 205, 206, 210–212, 221, 203
See application file for complete search history.

(56) References Cited

U.S. PATENT DOCUMENTS

2010/0195048 A1* 8/2010 Hammer et al. .............. 351/206

* cited by examiner

*Primary Examiner* — William Choi
*Assistant Examiner* — Sharrief Broome
(74) *Attorney, Agent, or Firm* — Patterson & Sheridan, LLP (57) ABSTRACT

Embodiments of the invention generally provide apparatuses and methods utilized in optics, and more specifically to apparatuses and methods for adaptive optics correction and imaging. Real-time wavefront sensorless adaptive optics correction and imaging is used with the living human eye to produce optical quality rivaling that of wavefront sensor based control in the similar systems. Using an optimization algorithm that is based on an image quality metric, the apparatus and method optimize the optical quality in ocular image frames acquired with an adaptive optics system.

35 Claims, 8 Drawing Sheets

WAVEFRONT SENSORLESS ADAPTIVE CORRECTION OF THE WAVE ABERRATION FOR AN EYE

BACKGROUND OF THE INVENTION

1. Field of the Invention

Embodiments of the invention generally relate to apparatuses and methods utilized in optics, and more specifically to apparatuses and methods for adaptive optics aberration correction and imaging. The invention disclosed herein relates to a method and system for sensorless adaptive optics that uses an optimization algorithm that is based on a suitable image quality metric to optimize the optical quality in ocular image frames acquired with a confocal adaptive optics scanning laser ophthalmoscope (AOSLO) or other image acquiring devices.

2. Description of the Related Art

Adaptive optics correction of the eye's optical aberrations enables high-resolution ocular imaging and measurement of visual function on a cellular level in living human eyes. Adaptive optics has been successfully incorporated in numerous ocular imaging modalities and has generated great potential for learning about, diagnosing, and treating diseases that impact the retina. Adaptive optics is an emerging technology that can correct for the eye's optical imperfections (or aberrations) to image the living eye and/or deliver vision testing stimuli with high resolution and precision. Adaptive optics has several research and clinical applications in normal and diseased eyes. The clinical importance of adaptive optics continues to grow as the number of scientific and clinical findings it has made possible in the eye continues to increase. Despite this potential, clinical translation and routine use of this technique outside the research laboratory has been slow.

A key feature of current adaptive optics systems for the human eye is a wavefront sensor that measures the eye's aberrations and is coupled in a closed feedback loop to a correcting element, such as a deformable mirror or liquid crystal spatial light modulator. In addition to increasing system complexity and cost, noise and fidelity of the wavefront sensor place a fundamental limit on achievable image quality in current adaptive optics ophthalmoscopes, since accurate aberration correction requires accurate measurement. This fundamental limit may be particularly adverse in the clinical environment, for patients with ocular pathology (such as cataracts or keratoconus), or in any other high noise situation (such as wavefront sensing with restricted light levels). Additionally, the wavefront sensor 'beacon' can interfere with visual experiments.

Thus, it would be advantageous to have a wavefront sensorless adaptive optics system for the living eye. However, the living human eye poses several unique characteristics that make it challenging to implement successfully wavefront sensorless adaptive optics techniques. Typically, wavefront sensorless correction methods have been implemented in situations where aberrations and the specimen being imaged are essentially static (e.g., in microscopy). This is quite unlike the situation in the living eye, where aberrations and tear film quality are inherently dynamic and eye movements create constant motion of the retina with respect to the imaging sensor. The dynamics of the eye's aberrations are exacerbated by the difficulty of stabilizing patients' pupils with respect to the optical system, while eye movements create the possibility that differences in intensity due to the spatial structure of the retina could create spurious differences in the intensity metric used for the sensorless control signal. These dynamics are especially problematic given the relatively large number of iterations that are desired for correction with sensorless methods. One of the current challenges in implementing wavefront sensorless adaptive optics in the human eye (given the temporal dynamics inherent in the eye's aberrations, which are not typically present in microscopy and other photonic engineering applications) is its relatively slow convergence speed. Blinking presents an additional challenge for effective sensorless adaptive optics methods.

Therefore, there is a need for improved apparatuses and methods for adaptive optics imaging, especially for apparatuses and methods suitable for the human eye.

SUMMARY OF THE INVENTION

Embodiments of the invention generally provide a wavefront sensorless correction system and method in which image quality is directly optimized based on physical properties of the image, which would be immune to noise or errors in the wavefront sensing process (as well as non-common path errors between the wavefront sensor and image plane). Real-time wavefront sensorless adaptive optics correction and imaging of the living human eye using the methods and systems described herein provides image quality rivaling that of wavefront sensor based control in similar systems. Embodiments provide algorithms to successfully achieve real-time imaging rates while dynamically correcting aberrations and suppressing the deleterious impact of blinking, including metric development for en face systems. Additional embodiments include the application to calibration and non-common path error calibration for wavefront sensor based systems, and the application to low light level or 'invisible' imaging (using an infrared light source that is invisible to the subject) and visual testing. An optimization algorithm, such as a stochastic parallel gradient descent algorithm, directly optimizes an image quality metric, such as the mean intensity, in ocular image frames acquired with an imaging device.

In embodiments of the invention, a probe beam of light, such as from a laser or superluminescent diode (SLD), is delivered to the eye and the reflected (or fluorescently emitted) light is collected. This light then forms an ocular image with its extent determined by the geometry of the incident probe beam. A metric of image quality is then computed from the image, and an optimization algorithm is used to adjust the shape of the correcting element to result in the best optical quality based on feedback obtained from monitoring this metric. An additional algorithm suppresses the optimization procedure in the event of signal loss, as occurs during blinks. The algorithms prevent the mirror from updating during sensorless control if the intensity in sequential image frames declines by a significant amount, such as by more than 50%.

In one embodiment, a method is implemented on a deformable mirror-based confocal scanning laser ophthalmoscope and uses the mean intensity of the light collected by the confocal pinhole as the metric. The metric value is averaged over a sufficient period of time to avoid spurious impacts of eye movement and retinal non-uniformity on the metric value, yet retain the ability to effectively correct the temporal fluctuations in the eye's aberrations. The deformable mirror is controlled by using a stochastic parallel gradient descent algorithm (SPGD) to optimize either the individual space of actuator voltages, or a set of modal compositions of actuator voltages, to result in the greatest value of the metric.

In another embodiment, the method is implemented in an en face (non-scanning) system and a double-pass point spread function (PSF) image is acquired with an imaging camera. An SPGD optimization algorithm controls the deformable mirror by using the fractional light within a user specified region of interest (ROI) from the camera as the image quality metric. The size of the adaptable ROI can be made smaller and smaller as the PSF shrinks in size due to increasing correction of aberrations. Other optimization algorithms that are based on a suitable retinal image quality metric also can be used to adjust the deformable mirror, liquid spatial light modulator, or other correcting element.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the Figures described below. It is to be noted, however, that the Figures illustrate only typical embodiments of the invention and are therefore not to be considered limiting of its scope, for the invention may admit to other equally effective embodiments.

DETAILED DESCRIPTION

Embodiments of the invention generally provide apparatuses and methods for adaptive optics imaging. Embodiments described herein provide real-time (e.g., 25 Hz), wavefront sensorless adaptive optics correction and imaging in the living human eye, with image quality either better or rivaling that of wavefront sensor based control in the similar or substantially similar systems. Wavefront sensorless correction methods where image quality is directly optimized based on physical properties of the image are immune to noise or errors in the wavefront sensing process (as well as non-common path errors between the wavefront sensor and image plane). In one embodiment, ocular aberrations may be corrected, typically for purposes of imaging the eye or performing visual studies, by controlling a correction device, such as deformable mirror or liquid crystal spatial light modulator, using a 'wavefront sensorless' method that does not utilize a wavefront measurement device. The wavefront sensorless method uses optimization techniques, such as an optimization algorithm that is based on a suitable image quality metric, to directly control the correcting device, which results in increased optical quality as determined by a suitable metric based on light exiting the eye. The method can also be applied to the measurement and calibration of 'non-common path errors' inherent in adaptive optics systems.

Wavefront sensorless correction methods described herein may also be utilized in ocular adaptive optics, and to image the retina of the human eye.

Figure 1:
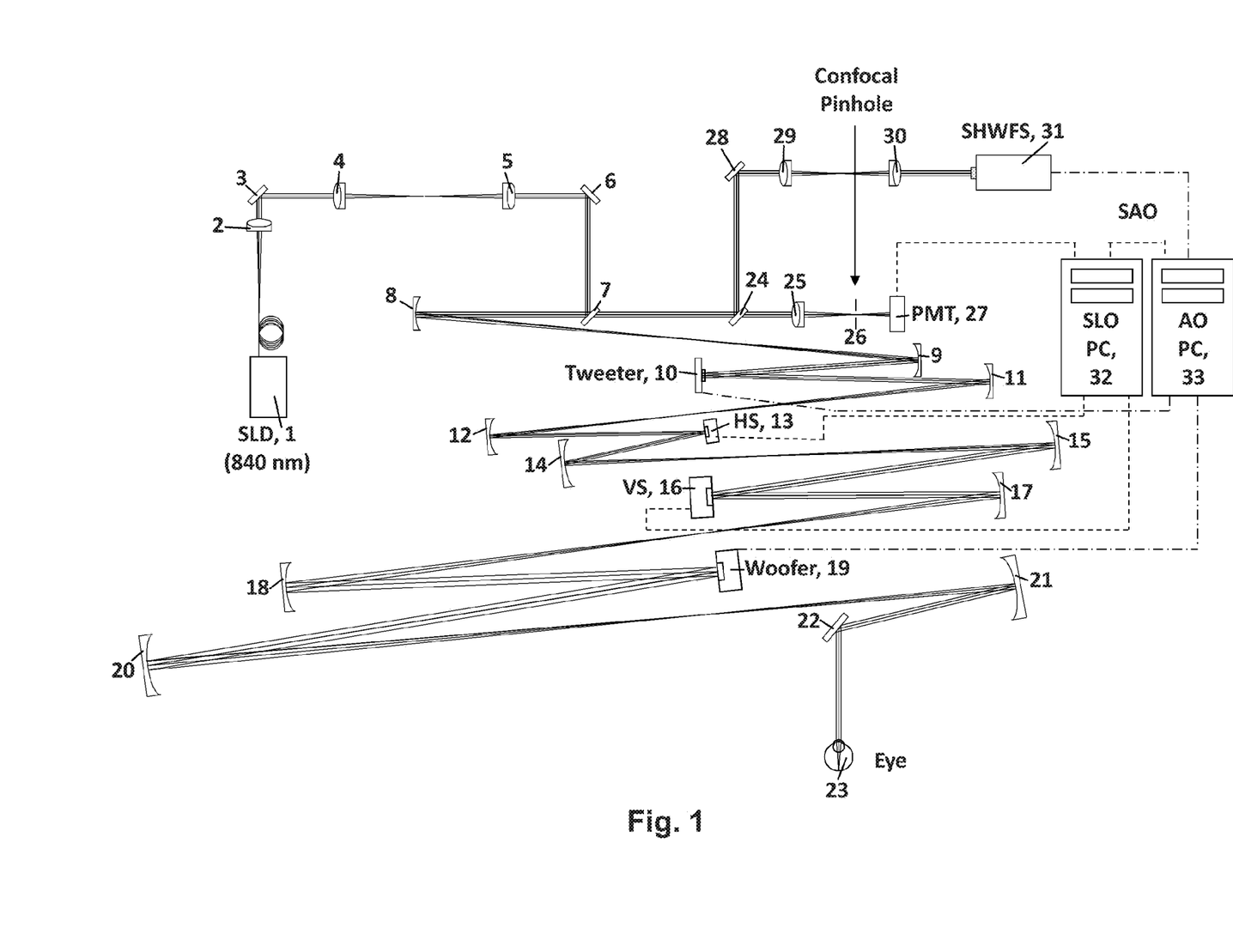
FIG. 1 depicts a schematic diagram of an embodiment of the sensorless adaptive correction system that uses two deformable mirrors as the correcting elements and a confocal pinhole image detection architecture.

One embodiment of the invention, shown in FIG. 1, uses an iterative stochastic parallel gradient descent (SPGD) algorithm to directly control the 140 actuator space of a microelectromechanical systems (MEMS) deformable tweeter mirror 10 (Boston Micromachines Inc., Cambridge, Mass.) in an AOSLO to maximize the mean intensity in the acquired retinal image frames. The mean image frame intensity is the average light reflected from the retina that passes through the confocal pinhole 26 (75 microns, angular subtense about 1.4') averaged over the system field of view (1.5 deg) during the frame exposure time (35 ms). This is an appropriate image quality metric since improving the optical correction yields a more compact point-spread function that enables more light to be focused and collected through the confocal pinhole.

In one embodiment, the AOSLO is a dual-mirror system that employs a 'woofer' 19—such as an electromagnetic deformable mirror (e.g., MIRAO® 52-e electromagnetic deformable mirror, available from Imagine Eyes, Inc., France)—to correct lower order aberrations and a tweeter mirror 10 (MEMS) to correct higher order aberrations. The woofer-tweeter arrangement is desirable if the MEMS mirror alone lacks sufficient stroke to correct individuals with significant refractive error. Prior to initiating adaptive optics control on the MEMS mirror 10, a Shack-Hartmann wavefront sensor 31 drives the correction of lower order aberrations (primarily defocus) using deterministic methods with the 'woofer' mirror. The 'woofer' mirror is subsequently not adjusted further while sensorless or wavefront sensor based control is implemented dynamically on the 'tweeter' mirror.

FIG. 1 depicts a schematic diagram of the AOSLO that has a Shack-Hartmann wavefront sensor (SHWFS) 31, a 52-actuator woofer mirror 19 (MIRAO® 52-e electromagnetic deformable mirror, available from Imagine Eyes, Inc., France), and a 140-actuator tweeter mirror 10 (Multi-DM MEMS mirror, Boston Micromachines Inc., Cambridge, Mass.), all in pupil conjugate planes. FIG. 1 is not drawn to scale, and those of ordinary skill in the art will recognize that the lenses, mirrors, and scanners depicted in FIG. 1 could be used in different combinations and at different angles to achieve the same effect. 840 nm light generated by a superluminescent diode (SLD) 1 (Superlum, Ireland) is projected through a series of lenses, mirrors, and scanners 2-22. The light generated by the SLD 1 passes through lens 2, is reflected by mirror 3, passes through lenses 4 and 5, and is reflected by mirror 6, 90/10 beam splitter 7, mirrors 8 & 9 and tweeter mirror 10. The light reflected from tweeter mirror 10 is reflected by mirrors 11 and 12 and scanned by a resonant horizontal scanner (HS) 13. The light is further reflected by mirrors 14 and 15 and scanned by a galvanometric vertical scanner (VS) 16. The light is then reflected by mirrors 17 and 18, and woofer mirror 19, before being reflected by mirrors 20, 21, and 22, after which it enters the eye's pupil through a maximum diameter of 8 mm and projects over a 1.5×1.5 degree patch of retina. The reflected light is descanned by VS 16 and HS 13 as it propagates back through the system (passing through, reflecting off of, or being scanned by items 7-22 depicted in FIG. 1) and about 20% is diverted by beam splitter 24 through mirror 28 and lenses 29 and 30 to the SHWFS 31 while the remaining light is focused by lens 25 through a confocal pinhole 26 (75 micron, 1.4°, about 1.6 times the width of the Airy disk with an 8 mm pupil) to a detector (photomultiplier tube, PMT) 27 for retinal imaging. One PC performs wavefront sensing and mirror control (AO PC) 33, using an optimization algorithm that is based on a suitable retinal image quality metric as described below, a second PC 32 acquires and records retinal image sequences (SLO PC). The PCs 32 and 33 operate independently during wavefront sensor based control but must communicate during sensorless control (SAO). An open loop correction of lower order aberrations (primarily defocus) is placed on the woofer mirror 19 with the SHWFS 31 prior to initiating closed loop correction with both control methods.

The tweeter mirror 10 is controlled by AO PC 33 using an optimization algorithm that is based on a suitable retinal image quality metric. Those of ordinary skill in the art will recognize that prior to the implementation of any adaptive optics control method, the woofer and tweeter in the described embodiment, or any correcting element used in the system, will need to be calibrated using software provided by the correcting element manufacturers, such as those available from Imagine Eyes or Boston Micromachines. These software products provide a software program in which the user determines how much the shape of the mirror will change in response to a particular applied voltage value. Such control algorithms are also described in, for example Chen L. "Control Algorithms (Chapter 5)". In: Porter J, Queener H, Lin J, et al., eds. *Adaptive Optics for Vision Science: Principles, Practices, Design, and Applications*. New Jersey John Wiley& Sons, Inc.; 2006, pp. 119-137.

In one embodiment, after calibration, the following algorithm can be used to determine the actuator control signals for the each iteration of the tweeter mirror 10 during the sensorless adaptive optics process:

$$u_i^{k+1} = u_i^k + (\Gamma J^k \Delta)(u_i^k \delta) \quad (1),$$

where $\Gamma$ is a gain parameter that determines the amount of voltage change applied in response to the observed intensity difference. For each iteration, k, an image quality metric ($\Delta J^k$) is computed by taking the difference in the mean retinal image frame intensity after adding, and then subtracting, a random perturbation ($\delta u_i^k$) to the control signal ($u_i^k$) of each of the i actuators. Thus, each iteration includes two image frames, each obtained immediately following a mirror update. Both mirrors are then held fixed over the duration of the acquired frame. The random perturbation is drawn with a uniform probability over the range $-\sigma$ to $\sigma$. Optimal performance of the SPGD algorithm may be accomplished by carefully pairing the gain ($\Gamma$) and perturbation ($\sigma$) amplitudes. The gain ($\Gamma$) and perturbation ($\sigma$) amplitudes empirically determined via systematic search to produce the highest image quality were similar in both model and human eyes and were also consistent with predictions from simulations.

Since this implementation utilizes two retinal image frames per iteration (FIG. 2A), the sensorless correction rate was half of the AOSLO's imaging rate (12.5 Hz). In some embodiments, sensorless control on only one of the AOLSO's mirrors can be implemented, however, in other examples, the SPGD sensorless control method is implemented on both mirrors for implementations utilizing dual-mirror systems. This could be achieved either sequentially or simultaneously by employing methods to decouple the mirrors' modal spaces similar to those already in use with simultaneous dual-mirror systems, such as that described in Li C., et al. "A correction algorithm to simultaneously control dual deformable mirrors in a woofer-tweeter adaptive optics system." *Opt Express*. 2010; 18: 16671-16684.

Figure 2A:
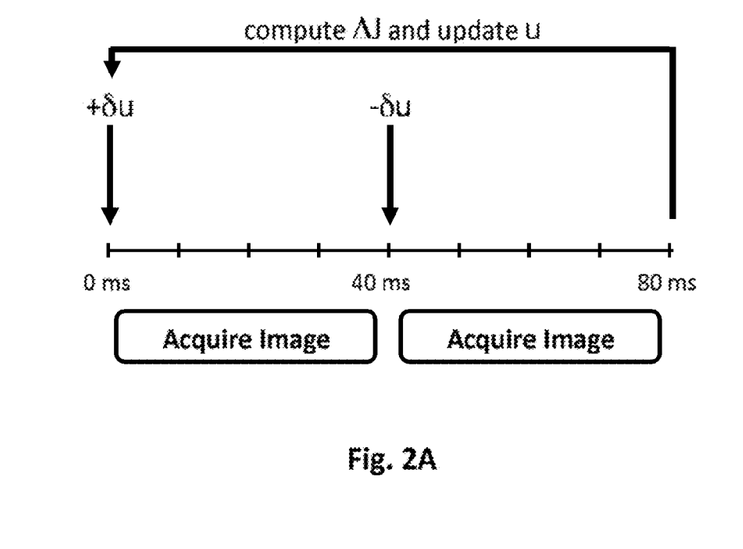
FIG. 2A depicts a correction timeline for one iteration of sensorless control, as described by some embodiments herein.
Figure 2B:
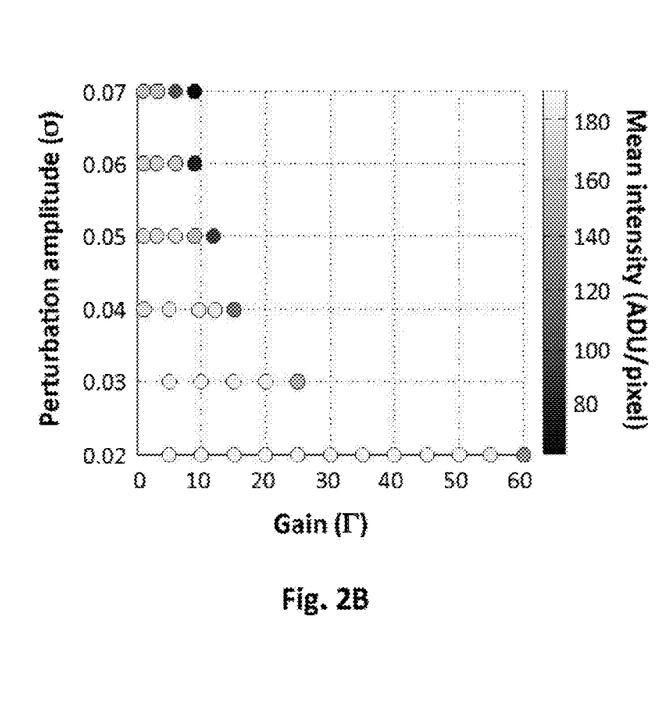
FIG. 2B depicts the image intensity obtained by a sensorless adaptive optics system, as described by some embodiments herein, wherein the image intensity is a function of gain and perturbation amplitudes.

FIGS. 2A-2B illustrate some details of the wavefront sensorless control algorithm. FIG. 2A depicts a correction timeline for one iteration of sensorless control. Exposure of the AOSLO image frames occur over 35 msec centered within each 40 msec interval (leaving a buffer for repositioning and settling of the vertical scanner between frames) and all desired calculations and mirror control occur within the first 3 msec at the start of each interval.

FIG. 2B, a graph of the results shown in Table 1 below, depicts how an optimal sensorless adaptive optics performance is accomplished by carefully pairing the SPGD control parameters. Mean image intensity after convergence for a model eye is displayed as a function of the gain ($\Gamma$) and perturbation ($\sigma$) amplitudes. Lighter shades denote higher intensities and darker shades denote lower intensities. Similar behavior was observed in human eyes for low perturbation amplitudes, in which a $\Gamma$ within a range from about 40 to about 60 and a $\sigma$ within a range from about 0.02 to about 0.03 generally provides the best correction with reasonable convergence times for an embodiment with a range of detector intensities from 0 to 255 ADU, and a voltage range for the correcting element from −1 to +1.

TABLE 1

| Correction Gain, $\Gamma$ | Perturbation Gain, $\sigma$ | Mean Intensity (ADU/pixel) for a PMT Gain of 0.328 |
|---|---|---|
| 1 | 0.04 | 180.5 |
| 1 | 0.05 | 178.3 |
| 1 | 0.06 | 174.7 |
| 1 | 0.07 | 165.1 |
| 3 | 0.05 | 181.6 |
| 3 | 0.06 | 175.8 |
| 3 | 0.07 | 167.3 |
| 5 | 0.02 | 192.2 |
| 5 | 0.03 | 190.1 |
| 5 | 0.04 | 186.8 |
| 6 | 0.05 | 182.3 |
| 6 | 0.06 | 172.2 |
| 6 | 0.07 | 109.9 |
| 9 | 0.05 | 167.0 |
| 9 | 0.06 | 79.1 |
| 9 | 0.07 | 64.1 |
| 10 | 0.02 | 193.3 |
| 10 | 0.03 | 191.4 |
| 10 | 0.04 | 187.7 |
| 12 | 0.04 | 186.3 |
| 12 | 0.05 | 95.4 |
| 15 | 0.02 | 192.3 |
| 15 | 0.03 | 191.2 |
| 15 | 0.04 | 127.2 |
| 20 | 0.02 | 193.7 |
| 20 | 0.03 | 190.7 |
| 25 | 0.02 | 194.0 |

TABLE 1-continued

| Correction Gain, Γ | Perturbation Gain, σ | Mean Intensity (ADU/pixel) for a PMT Gain of 0.328 |
|---|---|---|
| 25 | 0.03 | 158.1 |
| 30 | 0.02 | 193.6 |
| 35 | 0.02 | 193.8 |
| 40 | 0.02 | 193.3 |
| 45 | 0.02 | 193.3 |
| 50 | 0.02 | 191.7 |
| 55 | 0.02 | 186.4 |
| 60 | 0.02 | 140.3 |

Wavefront sensor based control uses deterministic methods, such as a simple integrator (gain=0.5) and a direct slope algorithm, as described above and in Chen L. "Control Algorithms (Chapter 5)", In: Porter J, Queener H, Lin J, et al., eds. *Adaptive Optics for Vision Science: Principles, Practices, Design, and Applications*. New Jersey: John Wiley & Sons, Inc.; 2006, pp. 119-137, to control the tweeter mirror (MEMs) at a rate of 10.5 Hz. This rate was predominantly determined by the wavefront sensor camera exposure and frame readout times (Rolera-XR, QImaging, Surrey, British Columbia). Sensorless adaptive optics allowed measurement and calibration of the non-common path errors between the wavefront sensor and imaging arms of the AOSLO. Calibration was accomplished by performing sensorless correction on a static model eye (contains a lens with a black matte reflecting surface in the nominal focal plane), and then using the Shack-Hartmann spot positions recorded during this empirically corrected state as the reference positions for subsequent wavefront sensor based correction. The rms wavefront error of the non-common path error obtained in this manner was about 0.05 microns over the system pupil, and was dominated by defocus (about 0.04 microns).

Figure 3:
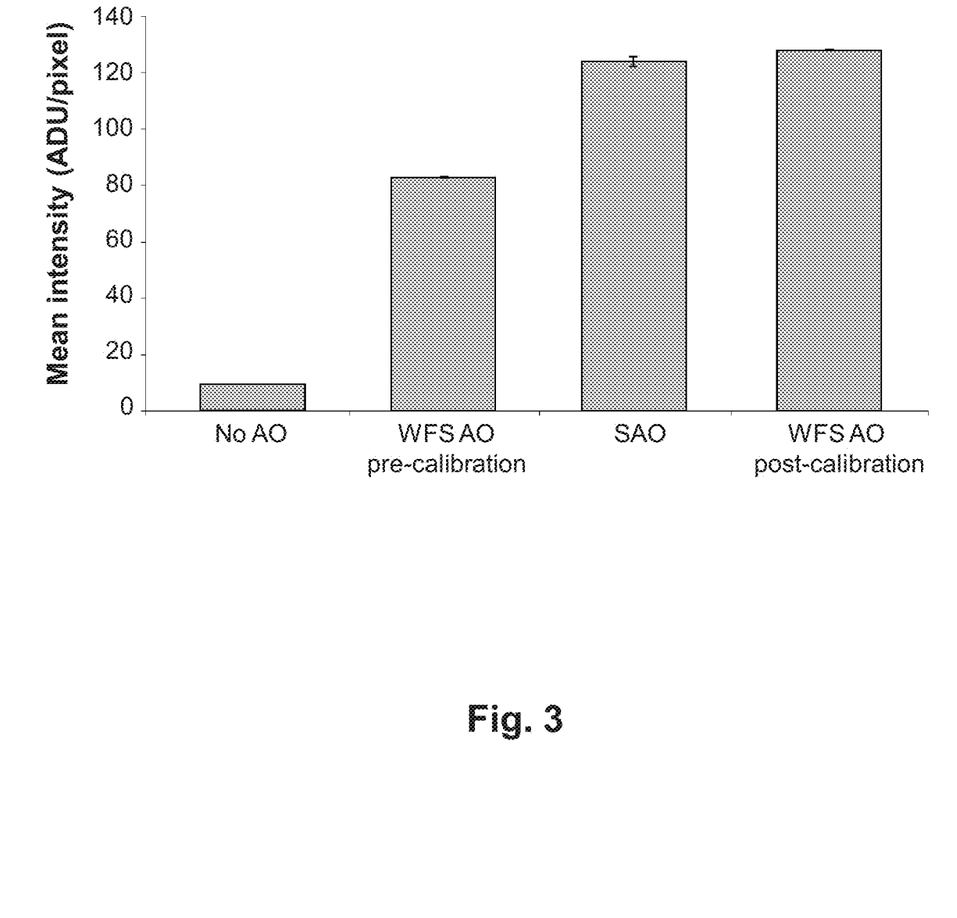
FIG. 3 illustrates the improved intensities obtained from the calibration using sensorless adaptive correction, per some embodiments described herein.

FIG. 3 illustrates the result of the calibration in the model eye: before calibration, the sensorless method outperformed wavefront sensor based control, while both methods performed comparably after calibration. This calibration for non-common path errors ensured that the comparatively good performance of sensorless adaptive optics observed was not due to suboptimal wavefront sensor based control or factors such as misalignment of the confocal pinhole.

FIG. 3 compares sensorless adaptive optics (SAO) control performance to non-common path error correction for wavefront sensor based adaptive optics in a model eye. Image intensities were 50% higher with sensorless control (SAO) than with traditional wavefront sensor based control (WFS AO pre-calibration). After using sensorless adaptive correction to calibrate for non-common path errors between the PMT and SHWFS (total rms wavefront error of about 0.05 microns over the system pupil), the performance of wavefront sensor based control (WFS adaptive optics post-calibration) improved to the level of sensorless control. Error bars are ±1 standard deviation of the mean image frame intensity after convergence. Note that absolute intensity cannot be compared with that in FIG. 2B due to different adjustments of the PMT gain between the two data sets.

The performance of the sensorless system described in FIG. 1 was compared to wavefront sensor based AOSLO corrections in five human subjects with no known ocular pathology. Subjects ranged in age from 32 to 40 years and refractive errors were as follows: S.30: −1.50 Dsph, −1.00 Dcyl; S.31: 0.50 Dsph, −0.25 Dcyl; S.49: 0.75 Dsph; S.62: 1.5 Dsph, −0.75 Dcyl; S.74: −2.25 Dsph, −0.25 Dcyl.

Multiple image sequences 30-100 seconds in length were first acquired at a rate of 25 Hz through each subject's natural, undilated pupil (3-6 mm diameter) with both sensorless and wavefront sensor based control. The subject's pupil was then dilated with 1 drop of 2.5% phenylephrine and 1 drop of 1% tropicamide and imaging was repeated through the full system pupil (8 mm). A static, lower order aberration correction was implemented with the system's 'woofer' mirror 19, such as an electromagnetic deformable mirror (e.g., MIRAO® 52-e electromagnetic deformable mirror), prior to initiation of closed-loop adaptive optics correction in all cases. A BMC MEMS deformable mirror dynamically corrected higher order aberrations using (1) a Shack-Hartmann wavefront sensor (WFS)-based control method (10 Hz) or (2) an SAO control method (12.5 Hz) in which the 140 MEMS actuator voltages were directly optimized via a stochastic gradient parallel descent (SGPD) algorithm to maximize the mean light intensity of AOSLO images. SGPD gain parameters were selected to yield optimal convergence speed and intensity. A blink rejection algorithm prevented the mirror from updating in a given iteration, e.g. adjusting or changing its shape, during sensorless control if the intensity in sequential retinal image frames differed by more than 50%. Averaged retinal images were created by registering and averaging 25 representative frames for each subject in each condition. Frames with the highest mean intensity and least eye movement were selected for registration. The relative performance of each control method was assessed by subjectively examining the average images. Performance was also assessed objectively by comparing the mean image intensity as a function of time and the radially-averaged power spectra of the averaged retinal images.

FIGS. 4A-L and 5A-L show that the retinal images acquired with sensorless control in living human eyes are of comparable quality to those obtained with conventional wavefront sensor based control in the same optical system. FIG. 4 illustrates a comparison of sensorless and wavefront sensor based control for AOSLO imaging though dilated (8 mm) pupils in 3 representative subjects. Images after sensorless adaptive optics (SAO,) (FIGS. 4A-C) and wavefront sensor based adaptive optics (WFS) (FIGS. 4D-F) were similar in all subjects. Images were acquired at about 1 degree eccentricity and are shown at the same scale. The scale bar in the image represents 10 minutes of arc. The center of the fovea was located approximately in the bottom left corner of FIGS. 4A-F. Despite typically lower image intensities and somewhat slower convergence (Intensity, FIGS. 4G-I), normalized image power spectra after sensorless control (red) were equal to or greater than those obtained with wavefront sensor based control (blue) (Power spectrum, FIGS. 4J-L).

Figure 4A:
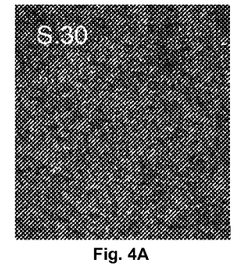
FIGS. 4A-C show retinal images acquired with sensorless control in living human eyes with dilated pupils in comparison to retinal images obtained with conventional wavefront sensor based control in the same optical system, FIGS. 4D-F, as described by some embodiments herein.
Figure 4B:
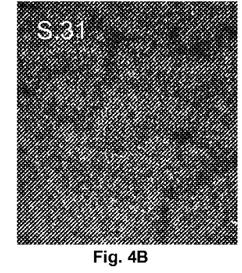
Figure 4C:
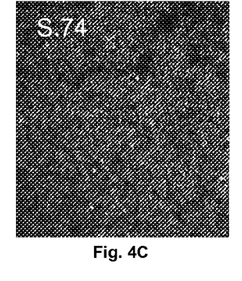
Figure 4D:
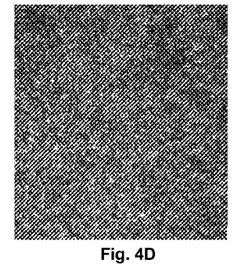
Figure 4E:
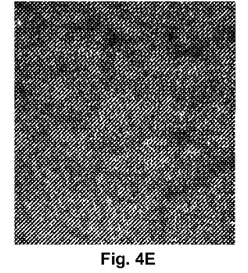
Figure 4F:
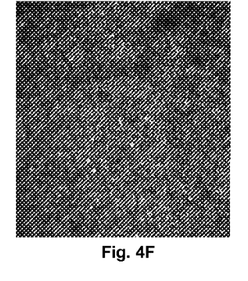
Figure 4G:
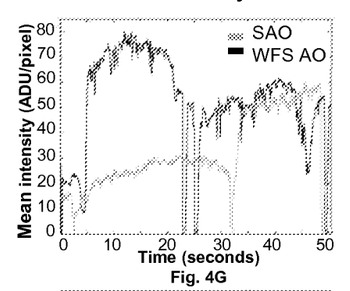
FIGS. 4G-I compare the mean intensity of the images obtained with sensorless and sensor-based control.
Figure 4H:
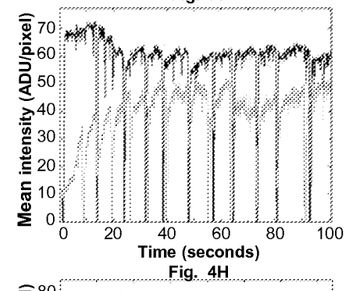
Figure 4I:
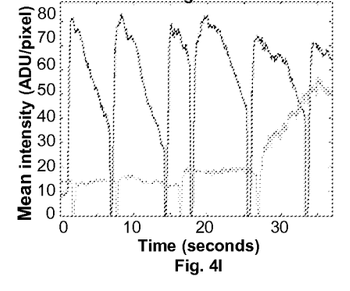
Figure 4J:
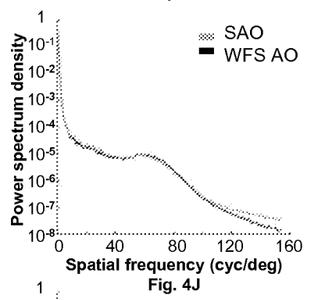
FIGS. 4J-L show the normalized image power spectrum for the images obtained.
Figure 4K:
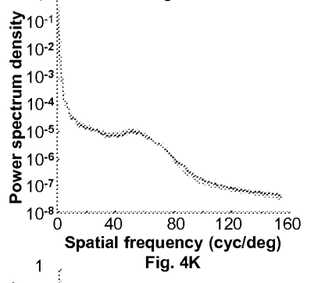
Figure 4L:
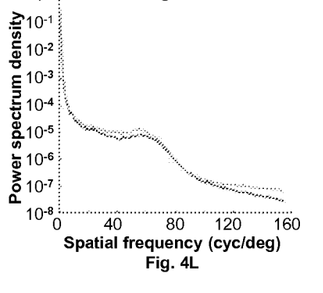

In FIGS. 4G-I, the sharp dips in the mean intensity traces are due to blinks or partial blinks. The gradual drop in intensity after recovering from blinks with WFS AO, such as in S.74, likely reflects instability or break-up of tear film. Note that the PMT gain was adjusted separately for each subject and pupil size, precluding direct comparison of absolute intensity values across subjects or between undilated and dilated pupils. Gain and perturbation amplitudes (Γ, σ) were as follows: S.30, (55, 0.02); S.31, (40, 0.03); S.74, (60, 0.02).

The good performance of sensorless adaptive optics was also evident when imaging through natural, undilated pupils (S.30, 6 mm; S.31, 4 mm; S.74, 6 mm) in the same 3 representative subjects. Images were acquired at about 1 degree eccentricity and are shown at the same scale. The scale bar in the image represents 10 minutes of arc. Sensorless control (FIGS. 5A-C) performed as well as wavefront sensor based control (FIGS. 5D-F) in terms of subjective image quality and mean image intensity. The center of the fovea is approximately located in the bottom left corner of FIGS. 5A-F. Both image intensity (Intensity, FIGS. 5G-I), and relative spectral power density (Power spectrum, FIGS. 5J-L) after sensorless control (red) compare favorably with wavefront sensor based control (blue). Results for all subjects were similar, with sensorless correction even allowing individual photoreceptors to be resolved in one subject whose small natural pupil (3 mm) precluded successful wavefront sensor based correction (presumably due to the difficulty in obtaining an accurate mirror control signal from a severely reduced set of Shack-Hartmann spots, FIG. 6).

Figure 5A:
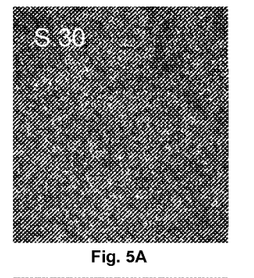
FIGS. 5A-C show retinal images acquired with sensorless control in living human eyes with natural, undilated pupils in comparison to retinal images obtained with conventional wavefront sensor based control in the same optical system, FIGS. 5D-F, as described by some embodiments herein.
Figure 5B:
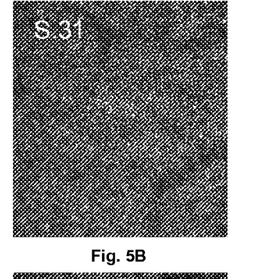
Figure 5C:
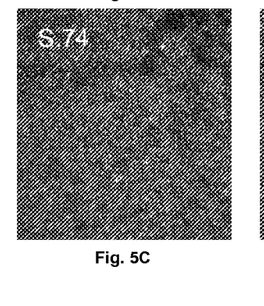
Figure 5D:
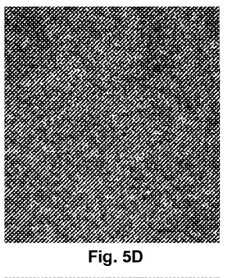
Figure 5E:
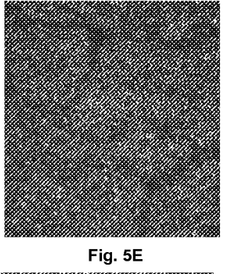
Figure 5F:
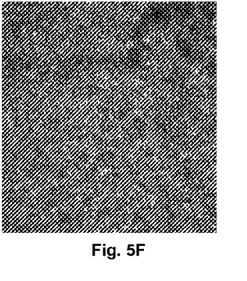
Figure 5G:
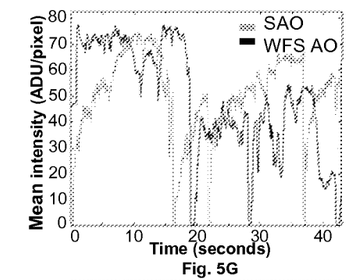
FIGS. 5G-I compare the mean intensity of the images obtained with sensorless and sensor-based control.
Figure 5H:
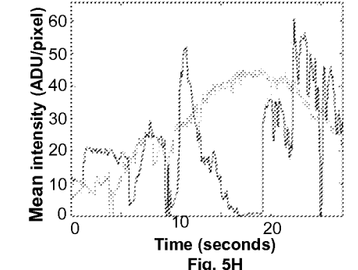
Figure 5I:
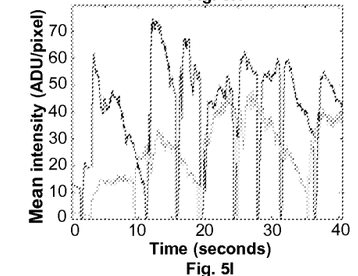
Figure 5J:
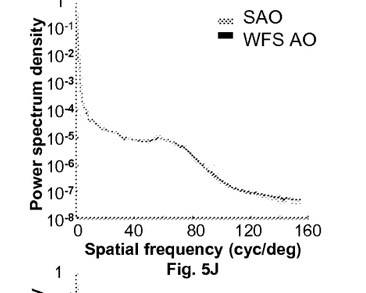
FIGS. 5J-L show the normalized image power spectrum for the images obtained.
Figure 5K:
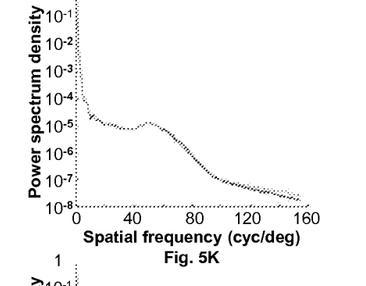
Figure 5L:
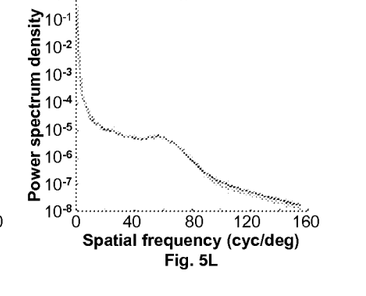

In FIGS. 5G-I, the irregularity of the mean intensity traces with wavefront sensor based control likely reflects difficulties in obtaining an accurate wavefront sensor based control signal with smaller, fluctuating, pupils, and likely also reflects tear film instabilities or break-up. The sharp dips in the mean intensity traces are due to blinks or partial blinks. Note that the PMT gain was adjusted separately for each subject and pupil size, precluding direct comparison of absolute intensity values across subjects or between undilated and dilated pupils. Gain and perturbation amplitudes ($\Gamma$, $\sigma$) for each subject were as follows: S.30, (60, 0.02); S.31, (50, 0.02); S.74, (60, 0.02).

The robust performance of sensorless adaptive optics for natural optics and pupils that underfill the AOSLO's entrance aperture (8 mm) indicates that sensorless methods can utilize less precise head stabilization and reduce the need for pharmacological pupil dilation, features that are highly advantageous in a clinically deployed system. Since image quality is directly optimized based on light exiting the pupil, and does not utilize pupil plane data to measure ocular aberrations, the method tolerates head movement and physiologically small pupil sizes, allowing high-resolution images to be acquired in individuals without pharmacological pupil dilation and/or in individuals for whom traditional adaptive optics correction fails.

Figure 6:
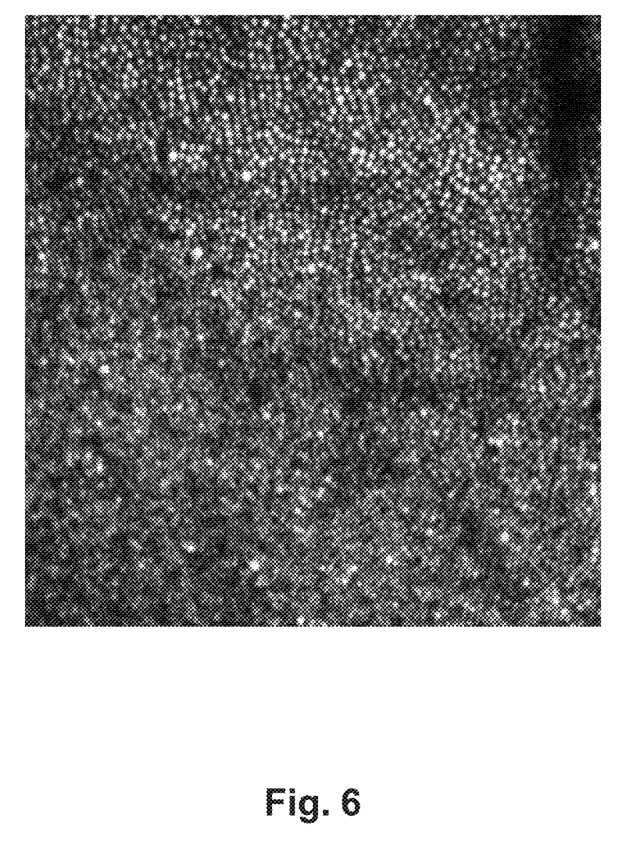
FIG. 6 illustrates one of the multiple clear images of individual photoreceptors acquired using sensorless adaptive optics, per several examples described herein.

FIG. 6 illustrates one of multiple clear images by sensorless adaptive optics allowed of individual photoreceptors to be acquired in one subject (S.62) when the pupil was sufficiently small (3 mm) as to prevent wavefront sensor based correction. Location and image details are the same as for FIGS. 4A-F and 5A-F. The scale bar in the image represents 10 arc minutes.

Figure 7A:
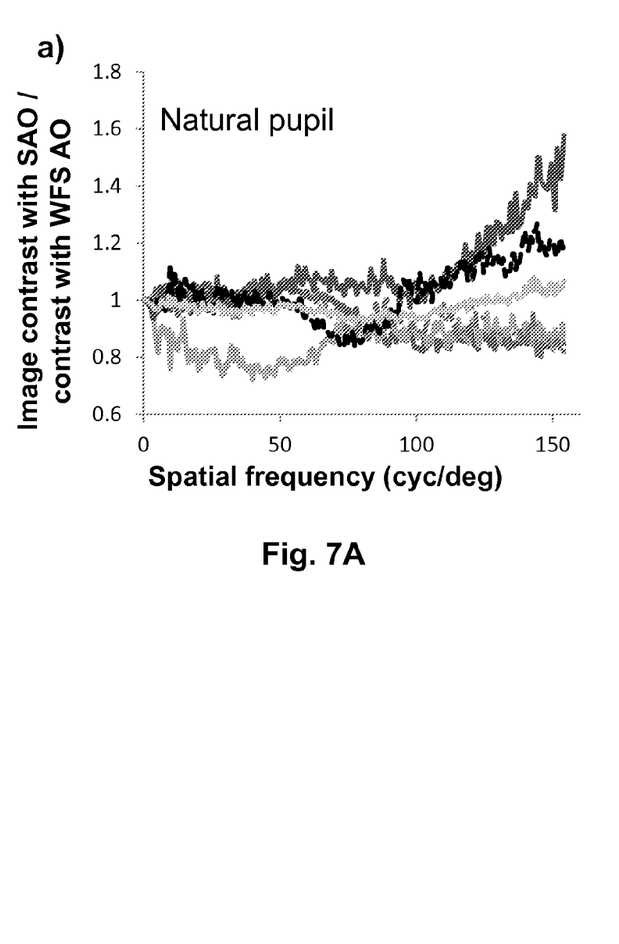
FIGS. 7A-7B depict ratios of the image contrast for averaged retinal images acquired with the sensorless control method to those acquired with traditional wavefront sensor based control, for undilated pupils, FIG. 7A, and dilated pupils, FIG. 7B, as described by some embodiments herein.
Figure 7B:
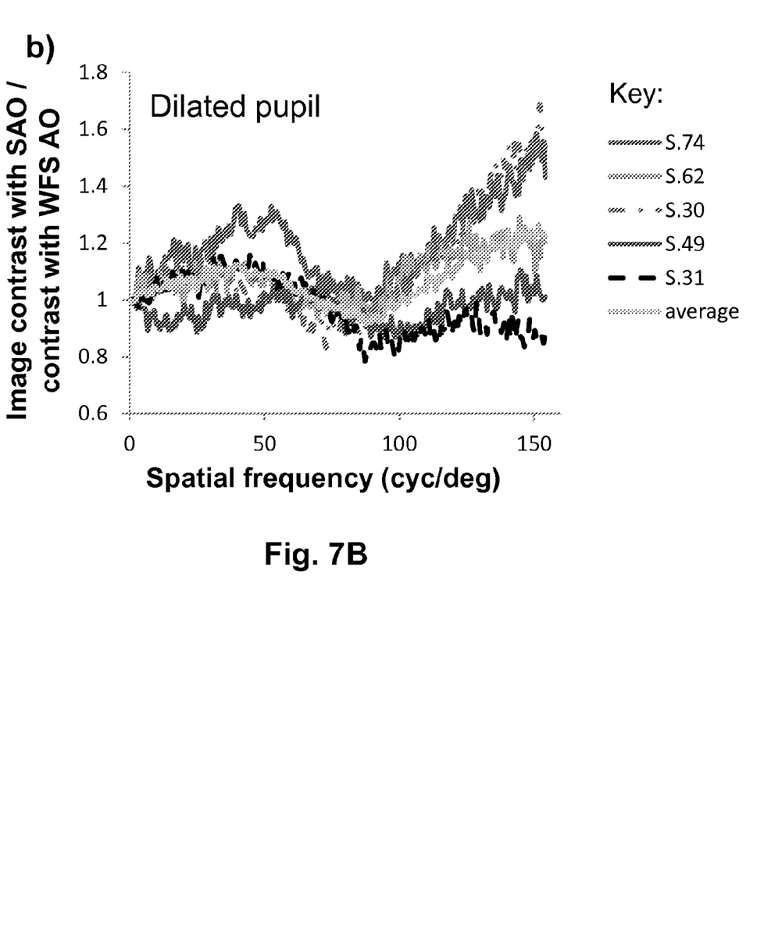

FIGS. 4A-L and 5A-L demonstrate that images taken with sensorless control are of comparable quality to those acquired with wavefront sensor based control despite typically having reduced image intensities (with dilated pupils) and utilizing increased time to reach the best correction. Normalized image power spectra, which are related to the square of the contrast at each spatial frequency, are similar in both methods. Image quality with sensorless and wavefront sensor based control was compared more quantitatively by plotting the contrast ratio for the averaged images acquired with both control methods as a function of spatial frequency in all eyes (FIGS. 7A-7B). When imaging through natural, undilated pupils (FIG. 7A), image contrast, on average, was not significantly different with sensorless than with wavefront sensor based control. However, when imaging through dilated pupils (FIG. 7B), image contrast tended to be higher with sensorless than with wavefront sensor based control, and this improvement was significant, on average. That sensorless control could produce higher contrast, but lower intensity, images reflects the tendency of the sensorless method, as implemented here, to generate light distributions with tight central cores often accompanied by broader 'wings' or halos. (This tendency was verified by observing the aerial double pass point spread function during sensorless correction with a model eye).

FIGS. 7A-7B depict ratios of the image contrast for averaged retinal images acquired with the sensorless control method to those acquired with traditional wavefront sensor based control in 5 subjects when imaging through natural undilated pupils (FIG. 7A) and dilated pupils (FIG. 7B). Dilated pupil size was 8 mm, undilated pupil size was approximately: S.30, 6 mm; S.31, 4 mm; S.49, 6 mm; S.62, 4 mm; S.74, 6 mm. Contrast ratios were calculated by taking the square root of the ratio of the normalized image power spectra. With natural pupils the contrast ratio averaged across subjects (black line) is not significantly different from 1, indicating that sensorless control yielded images of comparable contrast to those obtained with wavefront sensor based control. However when imaging through dilated pupils the contrast ratio averaged across subjects was greater than 1 at most spatial frequencies, indicating higher contrast with sensorless control. The average contrast improvement with sensorless control approached 25% at the highest spatial frequencies.

Convergence was slower with SAO than with WFS-based control. Mean image intensities after SAO and WFS-based control were similar in 4 of 5 undilated eyes, while mean image intensity was higher after WFS-based control in 4 of 5 dilated eyes. Despite similar or reduced intensities, the relative spectral power densities of AOSLO registered images were preserved or enhanced at higher spatial frequencies following SAO (compared to WFS-based control) in 4 of 5 eyes. SAO also successfully corrected 1 subject whose small natural pupil precluded successful WFS-based control. Assessment of non-common path errors with SAO indicated these were not responsible for its comparative success Because the image quality metric in the sensorless control implementation described herein is the light transmitted through the confocal pinhole averaged over the image frame duration (35 ms), the size of the confocal pinhole places a limit on the maximum optical quality that can be achieved. Once the optical correction results in all (or nearly all) of the light being focused through the pinhole, further improvements in optical quality no longer result in increases in light intensity, and will therefore not be effective at driving the sensorless algorithm. A confocal pinhole was utilized— wherein the confocal pinhole was subtending 1.4' at the retina, which is about 1.6 times the Airy disk diameter at 840 nm with an 8 mm pupil. The good performance achieved with this relatively large pinhole diameter suggests that even greater gains in contrast might be achievable with smaller confocal pinholes.

Figure 8:
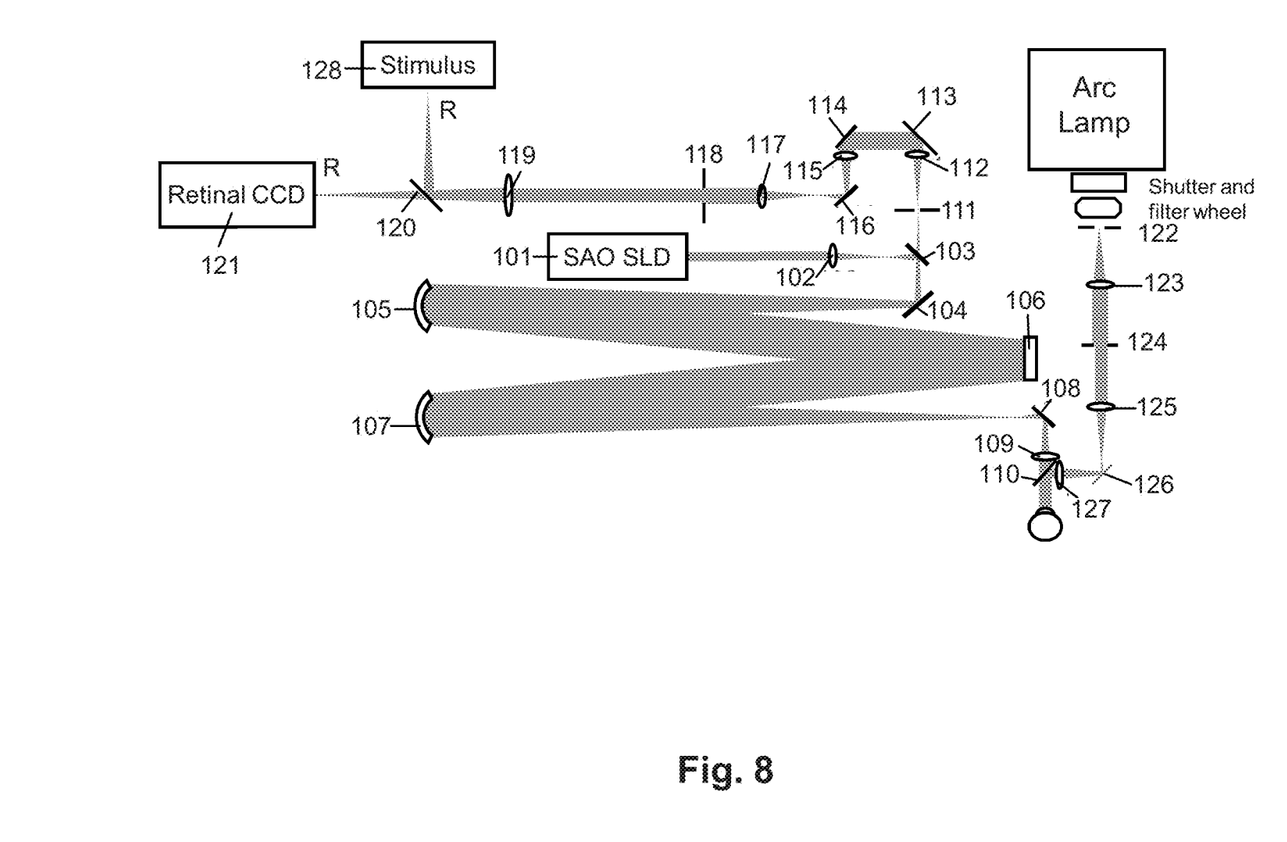
FIG. 8 depicts a schematic diagram of an embodiment of the sensorless adaptive correction system that uses one deformable mirror as the correcting element in a flood-illuminated adaptive optics system.

Another embodiment of the invention described herein is shown in FIG. 8. FIG. 8 uses an iterative stochastic parallel gradient descent (SPGD) algorithm to directly control the 97 actuator space of a Xinetics deformable mirror 6 in a flood-illuminated adaptive optics system to maximize optical quality of a visual stimulus or of acquired retinal images by increasing the compactness of the double-pass point spread function (PSF).

FIG. 8 depicts a schematic diagram of the flood-illuminated ophthalmoscope. FIG. 8 is not drawn to scale, and those of ordinary skill in the art will recognize that the lenses, mirrors, and scanners depicted in FIG. 8 could be used in different combinations and at different angles to achieve the same effect. 900 nm light is generated by a superluminescent diode (SLD) 101 and passes through lens 102, is reflected by beamsplitter 103 and mirror 104, is reflected by parabolic mirror 105, the deformable mirror 106, parabolic mirror 107, and mirror 108. The light then passes through lens 109 and 50:50 beamsplitter 110, after which it enters the eye through a maximum pupil diameter of 8 mm and is focused by the eye's optics to a spot. The reflected light propagates back through the system (passing through or reflecting off of items 104-110), after which a portion passes through beam splitter 103 where it continues to pass through aperture stop 111, lens 112, reflects off of mirrors 113 and 114, passes through lends 115, reflects off of mirror 116, passes through lens 117, aperture stop 118, lens 119, and beam splitter 120, forming an image of the double-pass PSF on a charge coupled device (CCD) camera (Retinal CCD, Princeton Instruments) 121.

The positions of the actuators of the deformable mirror 106 are adjusted using an SGPD algorithm with a suitable image quality metric, such as the fraction of the image intensity contained within a specified region of interest, derived from the recorded double-pass PSF image. Once the image quality metric achieves some predefined value, either a visual stimulus may be shown (Stimulus) 128, light from which reflects from beam splitter 120 and then propagates towards the eye as already described, or the eye may be exposed to illumination emitted from an arc lamp 122, which passes through lens 123, aperture stop 124, lens 125, reflects from mirror 126, passes though lens 127, and reflects from beamsplitter 110 and is projected over a 1 degree diameter on the retina. Light then reflects from the eye and propagates back through the system, as already described, and a retinal image may be acquired (also with the retinal CCD 21). Items 111, 121, 122, and 128 are in retinal conjugate planes. Items 106,118, and 124 are in pupil conjugate planes. In the alternative, the light used for correction may also be used for imaging or for stimulus generation.

Those of ordinary skill in the art will recognize that changes to the hardware or optical configuration of the system described herein will be possible but will still result in the same benefits described herein. These results should be easily replicable in other confocal systems (or non-confocal adaptive optics systems where double-pass point spread function imaging is enabled) with only relatively simple software changes in the mirror control algorithm that will be well known to those of ordinary skill in the art. Increases in speed and performance may be achieved with other hardware and software modifications, for example by using the time averaged PMT signal directly and integrating over a shorter interval of time (using smaller frames, or fractions of frames), using a smaller number of mirror, or Zernike, modes to control the mirror (rather than the 140 individual actuators), or by using an adjustable pinhole or detector with flexible integration area. The latter strategy may also be beneficial when correcting highly aberrated eyes in a wavefront sensorless system, as the pinhole size (or detector integration area) places a minimum requirement on optical quality to allow sufficient intensity to initiate correction. An initial scan through focus is another potential solution. For example, in highly aberrated eyes either a trial lens or Badal optometer could be empirically adjusted based on either the recorded image intensity (or wavefront image in wavefront-sensor-equipped systems) so as to begin sensorless correction with relatively little optical defocus. A more elegant approach would be to perturb the shape of the correcting element so as to add or remove various amounts of optical defocus, either systematically or adaptively, achieving a state of minimal optical defocus prior to initiating the sensorless algorithm to further improve optical quality.

The sensorless adaptive optics implementation described here has the additional property that it automatically focuses on the most reflective retinal layer. While this is advantageous in photoreceptor imaging or fluorescence imaging, it presents a further challenge for confocal or optical coherence tomography applications that allow for imaging of different retinal layers. The methods described herein are adaptable to be compatible with optical sectioning applications. For example, one could adjust the mirror rapidly to alternate frames used for sensorless control with imaging frames containing an appropriate defocus increment. The method can also be adapted to run sensorless control with reduced gain to maintain focus at a local intensity maximum corresponding to a non-photoreceptor layer in the retina of the eye.

Because sensorless control works well with small or undilated pupils, it would be particularly valuable in a clinical system so that dilation of pupils is not necessary. Sensorless control may also allow for the use of adaptive optics with individuals for whom traditional wavefront sensing is difficult or not possible, such as for patients with ocular pathology (such as cataracts or keratoconus). Sensorless control also utilizes less light for aberration correction and retinal imaging since no light is diverted from the image for wavefront sensing and all of the light returning from the eye is focused to only a single spot, rather than split up into hundreds of spots (as in a typical Shack-Hartmann wavefront sensor). Lower light levels are especially advantageous when imaging in light-sensitive patients, such as those suffering from rhodopsin disorders in retinitis pigmentosa, or with small children, and for applications, such as auto-fluorescence imaging, where sensorless control may confer additional benefit by allowing direct optimization of the fluorescence signal. Aberration correction and high-resolution imaging using lower light levels would also be beneficial for psychophysics applications or vision testing, especially for light-sensitive patients. Elimination of the wavefront sensor's "laser beacon" would also prevent any potential visual interference when presenting visual stimuli in functional experiments, enabling the full realization of adaptive optics' potential to uncover the most sensitive retinal and neural limits on vision.

Embodiments of the sensorless adaptive optics systems that do not use wavefront sensors would be simpler and cheaper than systems that use wavefront sensors.

The method described above could also use less than the entire image received to optimize image quality For example, the sensorless correction method described above may be applied in a scanning system where the detector has a variable effective aperture (for example electronically adjustable read area in a complementary metal-oxide semiconductor (CMOS) detector or an adjustable physical pinhole aperture in traditional detector systems). In this case, the method may be extended to allow the size of read area/aperture or region of interest to automatically decrease as the metric achieves some value (adaptive algorithm). Such adaptive algorithms extend the range of operation of the invention.

In another example, the sensorless correction method described above may be applied with a search space (optimization space) as the individual actuator space. In another example, the sensorless correction method described above may be applied with a search space being some modal composition of actuator patterns such as, but not limited to, the singular value modes of the mirror or Zernike modes.

While the foregoing is directed to embodiments of the invention, other and further embodiments of the invention may be devised without departing from the basic scope thereof, and the scope thereof is determined by the claims that follow.

What is claimed is:

1. A method of performing adaptive optics correction of an eye, the method comprising the steps of:
   a. causing light to enter the eye;
   b. receiving a first image of the light emitted or reflected from the eye;

c. computing a first image quality metric value for at least a portion of the first received image;
d. using an optimization algorithm that is based on an image quality metric to adjust a first correcting element to increase the computed image quality metric value for at least a portion of subsequently received images of the eye, wherein the optimization algorithm is a stochastic parallel gradient descent algorithm, wherein the stochastic parallel gradient descent algorithm is defined as:

$$u_i^{k+1} = u_i^k + \Gamma(\Delta J^k)(\delta u_i^k)$$

wherein $\Gamma$ is a gain parameter that determines the amount of voltage change applied to the first correcting element in response to a computed image quality metric value, $u_i^k$ is a control signal for an actuator that controls the first correcting element, $\delta u_i^k$ is a random perturbation applied to the control signal, and $\Delta J^k$ is a computed image quality metric value;
e. receiving a second image of the light emitted or reflected from the eye;
f. computing a second image quality metric value for at least a portion of the second received image; and
g. repeating steps a through f until a computed image quality metric value reaches a predefined value.

2. The method of claim 1, wherein received images are recorded at a rate of 25 Hz or greater.

3. The method of claim 1, wherein the correcting element is not updated if the computed image quality metric value is less than a minimum value.

4. The method of claim 3, wherein the minimum value is 50% of the previous computed image quality metric value.

5. The method of claim 1, wherein the method is applied to a confocal or scanning system.

6. The method of claim 1, wherein the image quality metric is mean intensity.

7. The method of claim 1, further comprising adjusting a second correcting element to increase the computed image quality metric value in a subsequently received image.

8. The method of claim 7, wherein a stochastic parallel gradient descent algorithm is used to adjust the second correcting element.

9. The method of claim 7, further comprising using a deterministic method to adjust at least one of the correcting elements.

10. The method of claim 7, wherein a wavefront sensor is used to adjust the second correcting element.

11. The method of claim 1, wherein $u_i^k$ is the control signal for some modal composition of actuator patterns for the first correcting element.

12. The method of claim 11, wherein the modal composition of actuator patterns comprise singular value modes or individual Zernike modes of the first correcting element.

13. The method of claim 7, wherein the first correcting element adjusts a set of modes and the second correcting element adjusts the remaining modes to increase the computed image quality metric value in a subsequently received image.

14. The method of claim 7, wherein one of the first and second correcting elements operates with a modal composition of actuator patterns and the other operates in the individual actuator space.

15. The method of claim 1, wherein the image quality metric is computed for a defined region of interest within each received image.

16. The method of claim 15, wherein the defined region of interest decreases as the computed image quality metric value moves toward a predefined value.

17. The method of claim 1, wherein the method is applied to a confocal imaging system such that the image quality metric is the total light collected through a pinhole.

18. The method of claim 17, wherein the size of the pinhole decreases as the image quality metric moves toward a predefined value.

19. The method of claim 1, wherein the method is applied to a line-scanning, or pinhole-less confocal system wherein at least one of the confocality and scanning are provided by reading and integrating the intensity in the received image from a predefined region of interest of at least one of a charged coupled device and a complementary metal-oxide-semiconductor camera.

20. The method of claim 1, wherein the image quality metric is the diameter that contains a defined fraction of the light in the received image.

21. The method of claim 1, wherein the first correcting element is not adjusted when the computed control signal exceeds a maximum criterion value.

22. The method of claim 1, wherein a received image is recorded when a computed image quality metric value reaches a predefined value.

23. The method of claim 1, wherein received images are recorded before and after a computed image quality metric value reaches a predefined value.

24. The method of claim 1, wherein modal methods are used to adjust the first correcting element while the computed image quality metric values are low and individual actuator methods are used to adjust the first correcting element as the computed image quality metric values increase.

25. The method of claim 1, wherein individual actuator methods are used to adjust the first correcting element while the computed image quality metric values are low and modal methods are used to adjust the first correcting element as the computed image quality metric values increase.

26. The method of claim 1, wherein the gain parameters are adjusted adaptively during correction.

27. The method of claim 1, wherein the method is applied to a wavefront-sensor-equipped system, wherein the wavefront sensor signals are used to place at least one correcting element in its initial state.

28. The method of claim 1, further comprising receiving an image comprising a defocus increment.

29. The method of claim 28, wherein the image comprising a defocus increment comprises the image of at least one layer other than the most reflective layer.

30. The method of claim 28, wherein the image comprising a defocus increment comprises a non-photoreceptor layer.

31. The method of claim 1, further comprising deriving an aberration from known aberrations of a sensor-based adaptive optics systems and the shape of the first correcting element to adjust the sensor-based system to allow it to be used with less light.

32. A method of calibrating a wavefront-based adaptive optics system, the method comprising the steps of
a. causing light to be reflected or emitted from a model eye;
b. receiving a first image of the light reflected or emitted from the model eye;
c. computing a first image quality metric value for at least a portion of the first received image;
d. using an optimization algorithm that is based on an image quality metric to adjust a first correcting element to increase the computed image quality metric value for at least a portion of subsequently received images of the model eye, wherein the optimization algorithm is a stochastic parallel gradient descent algorithm, wherein the stochastic parallel gradient descent algorithm is defined as:

$$u_i^{k+1}=u_i^k+\Gamma(\Delta J^k)(\delta u_i^k) \quad \quad 5$$

wherein $\Gamma$ is a gain parameter that determines the amount of voltage change applied to the first correcting element in response to a computed image quality metric value, $u_i^k$ is a control signal for an actuator that controls the first correcting element, $\delta u_i^k$ is a random perturbation applied to the control signal, and $\Delta J^k$ is a computed image quality metric value;

e. receiving a second image of the light reflected from the model eye;

f. computing a second image quality metric value for at least a portion of the second received image;

g. repeating steps a through f until a computed image quality metric value reaches a predefined value; and h. using an image obtained from the wavefront sensor as the reference wavefront image for subsequent wavefront-based adaptive optics correction.

33. A system for performing adaptive optics imaging of an eye or a model eye, the system comprising:
a light source;
a first correcting element;
a processor to record emitted or reflected light from an eye or a model eye and to compute an image quality metric value for the emitted or reflected light; and
a controller configured to control the first correcting element in response to the computed image quality metric value to increase the computed image quality metric value for the emitted or reflected light received by the recording and measuring means, wherein the controller uses an optimization algorithm to control the first correcting element, wherein the optimization algorithm is a stochastic parallel gradient descent algorithm, and wherein the stochastic parallel gradient descent algorithm is defined as:

$$u_i^{k+1}=u_i^k+\Gamma(\Delta J^k)(\delta u_i^k)$$

wherein $\Gamma$ is a gain parameter that determines the amount of voltage change applied to the first correcting element in response to observed computed image quality metric value, $u_i^k$ is a control signal for an actuator that controls the first correcting element, $\delta u_i^k$ is a random perturbation applied to the control signal, and $\Delta J^k$ is a computed image quality metric value.

34. The system of claim 33, further comprising a second correcting element.

35. The system of claim 33, wherein the image quality metric is mean intensity.

* * * * *

UNITED STATES PATENT AND TRADEMARK OFFICE
CERTIFICATE OF CORRECTION

PATENT NO. : 8,936,364 B2
APPLICATION NO. : 13/656380
DATED : January 20, 2015
INVENTOR(S) : Porter et al.

It is certified that error appears in the above-identified patent and that said Letters Patent is hereby corrected as shown below:

Title Page, (72) Inventors:

Please delete "Cracow" and insert -- Krakow -- therefor;

In the Specification:

Column 5, Line 52, please delete "$u_i^{k+1} = u_i^k + (\Gamma J^k \Delta)(u_i^k \delta)$" and insert -- $u_i^{k+1} = u_i^k + \Gamma(\Delta J^k)(\delta u_i^k)$ --, therefor.

Signed and Sealed this
Twenty-third Day of June, 2015

Michelle K. Lee
*Director of the United States Patent and Trademark Office*